United States Patent
Hierlemann et al.

(10) Patent No.: US 7,582,108 B2
(45) Date of Patent: Sep. 1, 2009

(54) TUBULAR IMPLANT

(75) Inventors: Helmut Hierlemann, Goeppingen (DE);
Maria Baumann, Goeppingen (DE);
Markus Milwich, Oberboihingen (DE);
Heinrich Planck, Nuertingen (DE)

(73) Assignee: Deutsche Institute für Textil-und Faserforschung Stuttgart Stiftung des Oeffentlichen Rechts, Denkendorf (DE)

( * ) Notice: Subject to any disclaimer, the term of this patent is extended or adjusted under 35 U.S.C. 154(b) by 627 days.

(21) Appl. No.: 10/973,824

(22) Filed: Oct. 27, 2004

(65) Prior Publication Data
US 2005/0143805 A1  Jun. 30, 2005

(30) Foreign Application Priority Data
Oct. 28, 2003 (DE) ................ 103 51 220

(51) Int. Cl.
*A61F 2/06* (2006.01)
(52) U.S. Cl. ................ 623/1.15; 623/1.2
(58) Field of Classification Search ........... 623/1.15, 623/1.22; *A61F 2/06*
See application file for complete search history.

(56) References Cited

U.S. PATENT DOCUMENTS

| | | | |
|---|---|---|---|
| 4,057,537 A | 11/1977 | Sinclair | |
| 4,655,771 A | 4/1987 | Wallsten | |
| 4,768,507 A | 9/1988 | Fischell et al. | |
| 4,799,479 A | 1/1989 | Spears | |
| 4,907,336 A | 3/1990 | Gianturco | |
| 4,950,258 A | 8/1990 | Kawai et al. | |
| 4,976,345 A | 12/1990 | Adrian et al. | |
| 4,990,155 A | 2/1991 | Wilkoff | |
| 5,306,286 A | 4/1994 | Stack et al. | |
| 5,500,013 A | 3/1996 | Buscemi et al. | |
| 5,540,713 A | 7/1996 | Schnepp-Pesch et al. | |
| 5,670,161 A | 9/1997 | Healy et al. | |
| 5,733,327 A | 3/1998 | Igaki et al. | |
| 5,762,625 A | 6/1998 | Igaki | |
| 5,906,641 A * | 5/1999 | Thompson et al. | 623/1.15 |
| 5,968,088 A | 10/1999 | Hansen et al. | |
| 5,968,092 A | 10/1999 | Buscemi et al. | |
| 5,980,564 A | 11/1999 | Stinson | |
| 6,007,574 A | 12/1999 | Pulnev et al. | |
| 6,080,177 A | 6/2000 | Igaki et al. | |
| 6,241,757 B1 | 6/2001 | An et al. | |
| 6,632,241 B1 * | 10/2003 | Hancock et al. | 623/1.15 |
| 2002/0087176 A1 * | 7/2002 | Greenhalgh | 606/155 |
| 2003/0100945 A1 * | 5/2003 | Yodfat et al. | 623/1.53 |
| 2004/0049260 A1 * | 3/2004 | Dong | 623/1.15 |

(Continued)

FOREIGN PATENT DOCUMENTS

DE    3 97 224 A    6/1924

(Continued)

*Primary Examiner*—Corrine M McDermott
*Assistant Examiner*—Jason-Dennis Stewart
(74) *Attorney, Agent, or Firm*—The Nath Law Group; Jerald L. Meyer; Sung-Yeop Chung

(57) ABSTRACT

The invention relates to a tubular implant, in particular a stent, in the form of a round braid composed of threads of biocompatible material extending in oppositely directed helices and crossing over each other, thread areas located at the tube ends being free from thread ends, and threads present there being guided back into the braid structure.

15 Claims, 4 Drawing Sheets

U.S. PATENT DOCUMENTS

| | | | |
|---|---|---|---|
| 2004/0167611 A1* | 8/2004 | Pulnev et al. | 623/1.15 |
| 2004/0172056 A1* | 9/2004 | Guterman et al. | 606/200 |
| 2005/0119684 A1* | 6/2005 | Guterman et al. | 606/198 |

FOREIGN PATENT DOCUMENTS

| | | |
|---|---|---|
| DE | 197 54 747 A1 | 6/1999 |
| DE | 197 50 971 A1 | 7/1999 |
| DE | 199 12 360 A1 | 9/2000 |
| DE | 100 23 099 C1 | 8/2001 |
| DE | 100 45 325 A1 | 4/2002 |
| DE | 101 28 376 A1 | 12/2002 |
| EP | 0 335 341 A1 | 10/1989 |
| EP | 0 797 963 A2 | 10/1997 |
| EP | 0 809 981 A1 | 12/1997 |
| EP | 0 857 471 A2 | 8/1998 |
| WO | 95/17859 A1 | 7/1995 |
| WO | 01/05331 A1 | 1/2001 |
| WO | 01/12256 A1 | 2/2001 |

* cited by examiner

TUBULAR IMPLANT

To treat defects in hollow cavities of the living organism, tube-like hollow structures called stents are implanted as endoprostheses. These are used to provide splint-like strengthening or support of hollow bodies in humans or animals. Typical application areas are, for example, the vascular system, the gastrointestinal system, and the urethral system. A catheter is normally used to bring stents in compressed form through the hollow body to be treated and as far as the desired site of treatment, where the stents are released. The deployment of the stent, compressed in the catheter, takes place via the inherent restoring spring forces resulting from the stent construction principle, or by means of balloon dilation. It is essential that the stents be able to participate, over a long period of time, in dynamic and static deformations, without experiencing any appreciable loss of their original restoring forces. In the ideal case, it is essential that the stent adapt to the implantation site in respect of lumen and in respect of flexibility and that it remain permanently as an implant in the body.

Numerous stents have been developed which are produced using metal materials, synthetic materials, bioabsorbable or non-bioabsorbable material, and a combination of materials, for example in the form of a coating.

U.S. Pat. Nos. 4,655,771, 4,768,507 and 4,907,336 describe self-expanding, non-absorbable stents. U.S. Pat. No. 4,990,155 discloses a thermoreversible, non-absorbable stent. EP 0,335,341 and U.S. Pat. No. 4,799,479 describe balloon-dilated, non-absorbable stents. U.S. Pat. Nos. 4,950,258 and 5,670,161 and EP 0,809,981 concern thermoreversible, absorbable stents. Self-expanding, absorbable stents are described in U.S. Pat. Nos. 5,980,564; 5,968,092; 5,500,013; 5,762,625; 6,080,177; 5,306,286; 4,057,537 and in Canadian patent 2,025,625 and EP 0,797,963.

In clinical use, the stents presently available on the market continue to show unfavorable characteristics and undesired clinical results, for example material fatigue, stent dislocation, inflammation, thrombosis or restenosis. These disadvantages adversely affect the outcome of treatment and the lasting nature of the treatment, to the detriment of the patient.

The object is therefore to make available an improved stent which overcomes the inadequacies of stents from the prior art and is easy and safe to use.

This object is achieved by a tubular implant, in particular a stent, in the form of a round braid composed of threads of biocompatible material extending in oppositely directed helices and crossing over each other, wherein the tube ends are free from thread ends, and threads present there are guided back into the braid structure. In contrast to known stents which are cut from long tubes or hoses and therefore have interfering thread ends at the ends of the tube, such thread ends are not present at the tube ends of the stent according to the invention. It is therefore also not necessary to cover such thread ends or bind them into another material. Braid is preferably to be understood as meaning diagonally extending threads crossing over and under each other.

In this way, it is possible to overcome the disadvantages of conventional stents which are produced by braiding technology and consist of a multiplicity of monofilament or multifilament threads or yarns in which, after the production process, there are numerous blunt or sharp cuts and raw edges of the open thread ends, which require secondary treatment by coating, soldering, welding or laminating in order to avoid their trauma-inducing effect.

According to the invention, the tubular implant can be characterized by having a radially compressible and expandable and also axially flexible tube structure. In the unstressed state, i.e. without the action of external radial forces, the stent has a radially uniform tube-like shape. The implant can preferably be flexible in the radial and axial directions.

The implant according to the invention can be advantageously made of threads which are monofilaments. The monofilaments can have a diameter of 30 µm to 2 mm, in particular 70 µm to 500 µm. In a further refinement, parallel filaments can be slightly twisted with one another.

In a particular embodiment of the invention, the braid of the implant is formed from a single thread, that is to say a so-called continuous thread. A self-expanding stent made of an in particular single monofilament has a net-like braid structure.

In a further particular embodiment of the invention, the braid of the implant can be formed from two parallel, preferably oppositely directed monofilaments (double strand) and preferably, also in the formation of the braid, from a single continuous thread.

The thread intersection angle α (cf. FIG. 1) in the braid between intersecting monofilaments can be greater than 45°, in particular 70 to 150°, and preferably 90 to 120°. According to the invention, the filaments can be bent at the implant ends, in particular configured in a curve shape or serpentine shape. Thread ends, in particular the two ends of the single thread, can preferably lie in the circumferential plane or circumferential surface of the round braid. Moreover, thread ends, in particular all of the thread ends, can lie close to one another in the respective helix and preferably point in opposite directions.

According to the invention, it may be advantageous that the thread areas are turned back at at least one tube end and are guided back in helical formation in the plane of the braid. In a particular embodiment, thread areas at least at one tube end, in particular at one tube end, can be turned back in a loop shape, forming a U-turn, and are guided back in the same helix. In one embodiment, thread areas at at least one tube end, in particular at one tube end, can be guided back at an angle of 60 to 120°, in particular ca. 90°, and in an oppositely directed helix. Thread areas at at least one tube end, in particular at one tube end, can preferably be turned back at 150 to 300°, in particular ca. 270°, forming a cross-over loop, and are guided back in an oppositely directed helix.

According to the invention, at at least one tube end, in particular at one tube end, one thread area can preferably be turned back at 60 to 120° and one thread area from the same helix can be turned back at 150 to 300° as a cross-over loop, and the looped thread can be guided back in the directly contiguous return helix, and the thread turned back only in a U-shape can be guided back in the succeeding parallel return helix. An example of such a configuration is shown in attached FIG. 4.

The tubular implant according to the invention can further be characterized by being designed as a lattice and, in the unstressed state, having a lattice width of 0.5 to 8 mm, in particular 2 to 5 mm. The thread intersection angles can be more than 45°, in particular 70 to 150°, preferably 90 to 120°.

In a preferred embodiment, each helix in the braid of the implant according to the invention is made up of at least two threads, in particular two threads lying parallel alongside one another. In particular, when a helix has a thread count which is an even number, two threads lying alongside one another can in each case extend in opposite directions at a stent end. An example of such a configuration is shown in attached FIG. 5.

According to the invention, in one embodiment the braid structure can have a thread profile of 1 over 1, 1 under 1. In another embodiment, the braid structure can have a thread profile of 2 over 2, 2 under 2. Relative to the cross section of the stent, 4 to 16, in particular 6 to 12, helices can advantageously be provided in each helix direction.

According to the invention, the tubular implant can be designed with a radially constant diameter. In a particular embodiment of the invention, the tubular implant can be narrowed at the end, that is to say have a smaller diameter at the end. Such a narrowing of the stent can be expedient for the purpose of filtering, e.g. in the blood stream. In another preferred embodiment of the invention, the tubular implant in the stressed state can be bulged at the extremities, that is to say have a greater diameter at at least one end, preferably at both ends, than in the middle area. Such radial expansion may be expedient to avoid dislocations after introduction of the stent.

In the tubular implant according to the invention, at least one of the implant ends can have a radially divergent design. In other words, in one embodiment of the invention one end of the tubular implant can be widened. In another embodiment of the invention, both ends of the tubular implant can be widened. The transition from the linear part of the implant to the divergent end can advantageously be stepless. Such a widening of the diameter can be funnel-shaped or tulip-shaped.

In the implant according to the invention, the biocompatible material can be metal. Typical examples are metal filaments made of titanium, titanium alloys, medical-grade stainless steel, such as Cr—Ni steels, W1.4310, Elgiloy®, Phynox®, iridium or metal oxide alloys. So-called shape-memory metals, e.g. Nitinol®, can also be used.

In another embodiment of the invention, the biocompatible material can be synthetic polymer material. Typical examples are filaments made of synthetic polymers such as polyethylene terephthalate (PET), polyurethane (PUR), polypropylene (PP), high-density polyethylene (HDPE), polyamide, copolymers, blends or mixtures of such polymers. For absorbable implants or absorbable parts of implants, it is preferable to use polymers based on α-polyhydroxycarboxylic acids, β-polyhydroxycarboxylic acid or poly-anhydrides in the form of their homopolymers, copolymers, terpolymers, block polymers or mixtures thereof.

In a particular embodiment of the invention, the biocompatible material can be a combination of different materials, in particular a composite. Typical examples are blend polymers, bicomponent monofilaments, such as monofilaments with a core/mantle structure, metal/polymer composites, in particular with metal matrix, and also polymer-coated metals. The thread material of the stents can have a surface coating of metal, especially if the thread material is a polymer.

Numerous filament modifications can be employed, as is appropriate to the desired application purpose. For example, structured monofilaments, hollow capillary monofilaments, coated monofilaments with single-layer or multi-layer coating. Thus, the monofilaments can have a structured cross section, e.g. a star-shaped cross section or a cross section with core/mantle structure.

The filament material used according to the invention can lie within a wide range of fiber strengths and fiber thicknesses (filament diameters). Diameters of 10 to 800 µm, in particular 30 to 300 µm, are preferred for metal filaments, and diameters of 30 to 1000 µm, in particular 50 to 500 µm, for polymer filaments.

In one embodiment of the invention, the biocompatible material can be non-bioabsorbable. In another embodiment of the invention, the biocompatible material can be at least partially bioabsorbable. In yet another embodiment of the invention, the biocompatible material can be completely bioabsorbable.

The monofilaments for forming the braid structure of the tubular implant can advantageously have a high tensile strength in the range above 100 N/mm$^2$ and/or a high modulus of elasticity in the range above 500 N/mm$^2$.

The tubular implant of the invention can advantageously be characterized by being elastic and/or plastic. The elastic and/or plastic properties are based on the combination, according to the invention, of monofilament and braid structure.

In a further refinement, the originally open-pore braid structure of the tubular implant can be covered at least partially on the inside and/or outside by a lining. In another embodiment, the originally open-pore braid structure can be covered at least partially on the inside and/or outside by a coating. Materials with elastic and/or plastic properties can advantageously be used as coating.

A coating can completely embed the implant according to the invention. Alternatively, only certain parts of the implant can be provided with a coating, for example one or both ends. The coating can cover only the thread material, so that the diamond-shaped openings of the braid are left uncovered. Especially in the case of elastic coating material, the coating can also close the implant wall. The coating can be in the form of a covering, in which case the tubular implant is drawn onto an already preformed envelope or a film and thus covered inside and/or outside. In another procedure, a coating can be formed by means of structural elements of the tubular implant entering into an intimate physical and/or chemical connection with a coating material. The coating material can be absorbable.

According to one embodiment of the invention, the covering and/or the coating can be bound adhesively. According to another embodiment of the invention, the covering and/or the coating can be covalently bound.

In one refinement, the implant according to the invention can advantageously be provided with at least one additive. The additive can, in particular, be a pharmacological active substance. Examples of such additives are agents for improving antithrombogenicity, such as hirudin, prostacyclin, and heparin. When the implant according to the invention is used as a drug delivery carrier for active substance release, additives such as anticancer agents, for example Taxol® or Thalomid® can be added. In another embodiment, the additive can be an X-ray marker. A coating or covering of the thread material can be formed in particular for a drug delivery.

In one special embodiment, the additive can be living cells.

In the implant according to the invention, additives can advantageously be incorporated with the aid of coating technologies. Depending on the choice of active substances and on the coating method, it is possible to dope additives on the surface and/or introduce them into the polymer matrix. In this way, the release of one or more added substances can be controlled via the degradation behavior and/or absorption behavior of the polymer material used.

The invention also relates to a method for producing a tubular implant made of biocompatible material in monofilament form by textile braiding methods to form a flexible, tubular braid with a closed structure at the ends. To form the tubular implant according to the invention, the braiding can advantageously be carried out over a mandrel. In a preferred refinement, the braiding is done by machine, in particular automatically. The raw braid can undergo secondary shaping, thermal aftertreatment (tempering), covering, coating, or any desired combination of such operations. The raw braid for the tubular implant can preferably undergo thermal aftertreatment.

The advantage of the production method according to the invention is that an atraumatic braid construction, closed at the distal and proximal ends, is obtained. In this way, lining of the stent ends and similar subsequent working is unnecessary.

A tubular implant according to the invention is advantageously suitable for use in the treatment of pathologically altered defect sites in hollow organs in human medicine and veterinary medicine. Possible examples are: malignant and benign obstructions, stenoses, protuberances (aneurysms) and lesions on hollow organs. Typical areas of use for stents according to the invention are blood vessels, esophagus, trachea, duodenum, colon, and other parts of the digestive system, urinary tract and ureter. The tubular implant according to the invention can be used particularly advantageously on hollow organs in the vascular, gastrointestinal, tracheobronchial and/or urethral regions.

The tubular implant according to the invention is suitable for supporting and/or keeping open a human or animal hollow organ for a defined time interval or permanently. This time interval depends on the chosen material and can be precisely set according to the medical requirement. With the implant according to the invention, mechanical and physiological requirements, such as diameter, restoring force, compression force and flexibility, can also be very precisely set.

For practical application, the tubular implant according to the invention can be compressed with commercially available catheters, brought to the treatment site, and positioned in situ using conventional release systems. By virtue of its structure, the tubular implant according to the invention is self-expanding and is pressed with a suitably chosen restoring force against the hollow organ that is to be treated.

The present invention is explained below by describing particular embodiments on the basis of examples and with reference to the attached drawings. In these embodiments, individual features of the invention can be realized alone or in combination with other features. Where a particular embodiment is described, this serves only to explain and provide a better understanding of the invention and is not in any way to be understood as limiting the invention.

In all the figures, two monofilaments are in each case guided in pairs in the helices of the braid, as is preferred.

EXAMPLE 1

Stent for the Esophagus/Trachea Region

Figure 1:
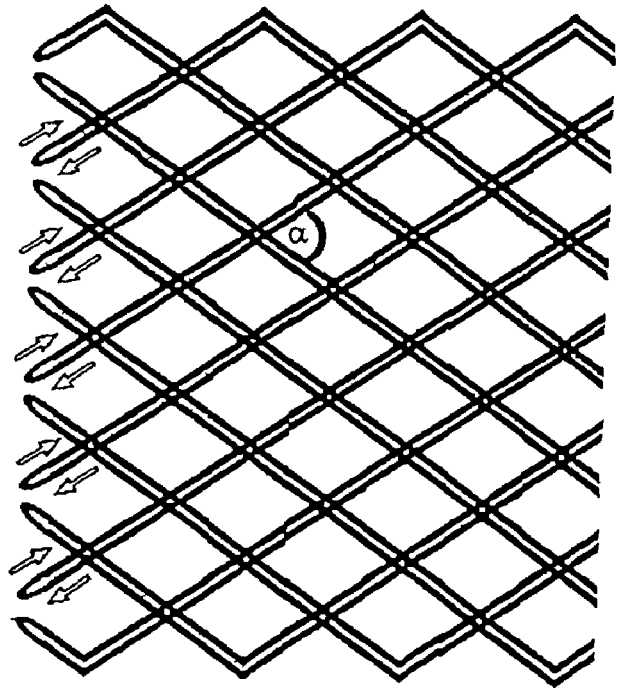
FIG. 1 shows an end portion of an uncompressed tubular stent. The arrows indicate displacement possibilities of the monofilaments in the braid structure of the tubular implant according to the invention. The symbol α designates the thread intersection angle in the braid. At the stent end, the monofilaments are turned back and are guided back in the same helix.
Figure 2:
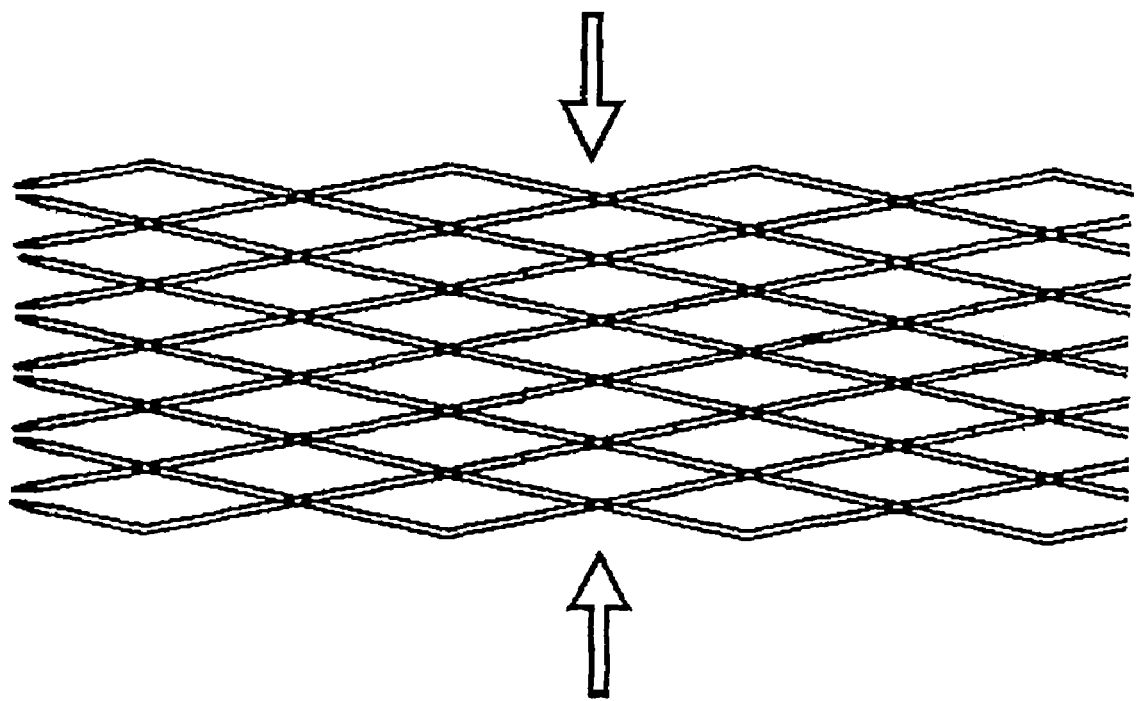
FIG. 2 shows the stent according to FIG. 1 under radial compression and axial dilation. The arrows indicate the action of the force of compression.
Figure 3:
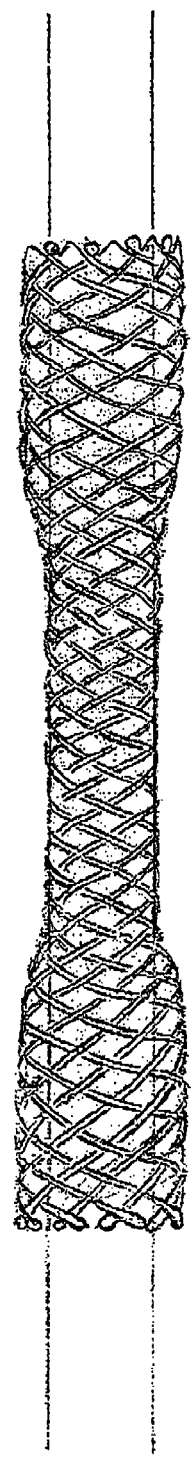
FIG. 3 shows a fully formed tubular stent with divergent extremities at both ends, that is to say with tulip-shaped widenings at the distal end and proximal end. This embodiment is described in Example 1. The two ends of the tube show a different return of the threads in the circumferential plane of the tubular braid. The braid consists of a single monofilament thread. The two concealed thread ends, which can be connected to one another, lie in the circumferential surface of the braid.
Figure 4:
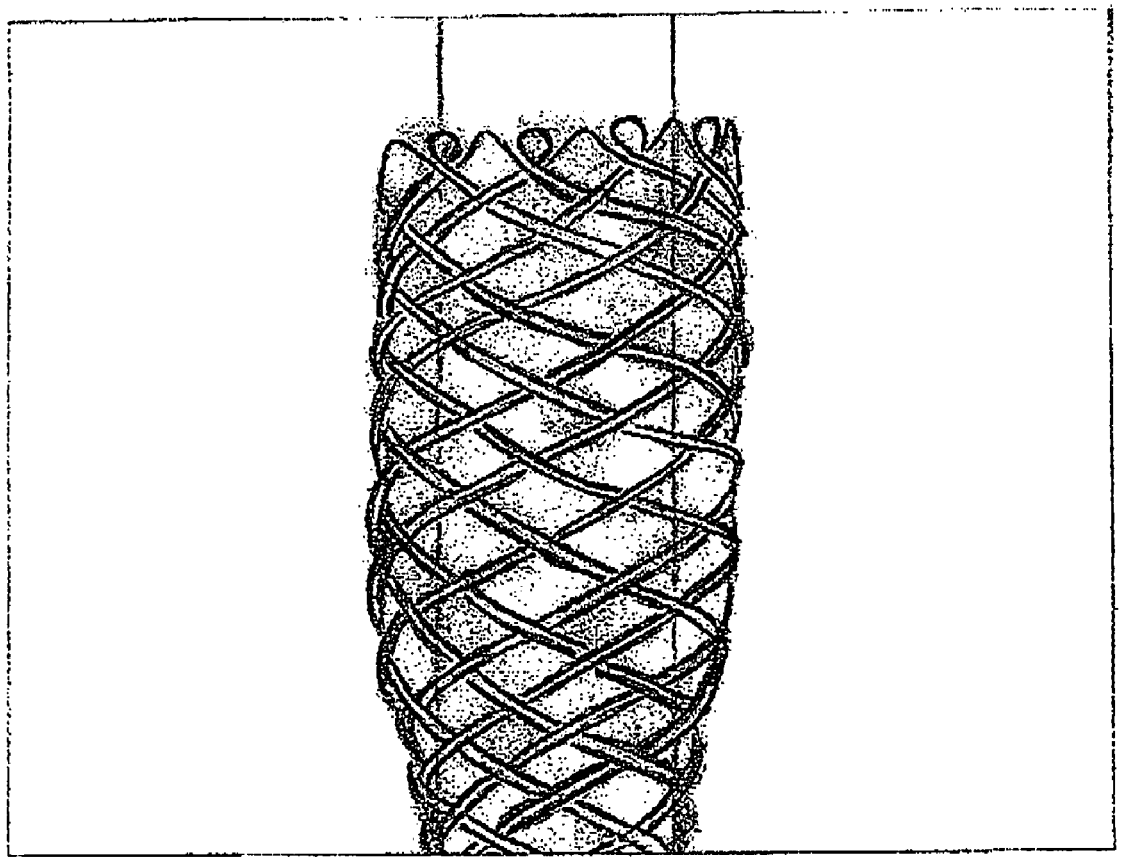
FIG. 4 shows, in another embodiment, the filament profile at the end of the braided stent, in particular at one end (the upper end) of the stent according to FIG. 3. The loop formations can clearly be seen, so that no free thread ends protrude at the end. Thread areas angled in a U-shape and thread areas formed as cross-over loops alternate at the tube end.
Figure 5:
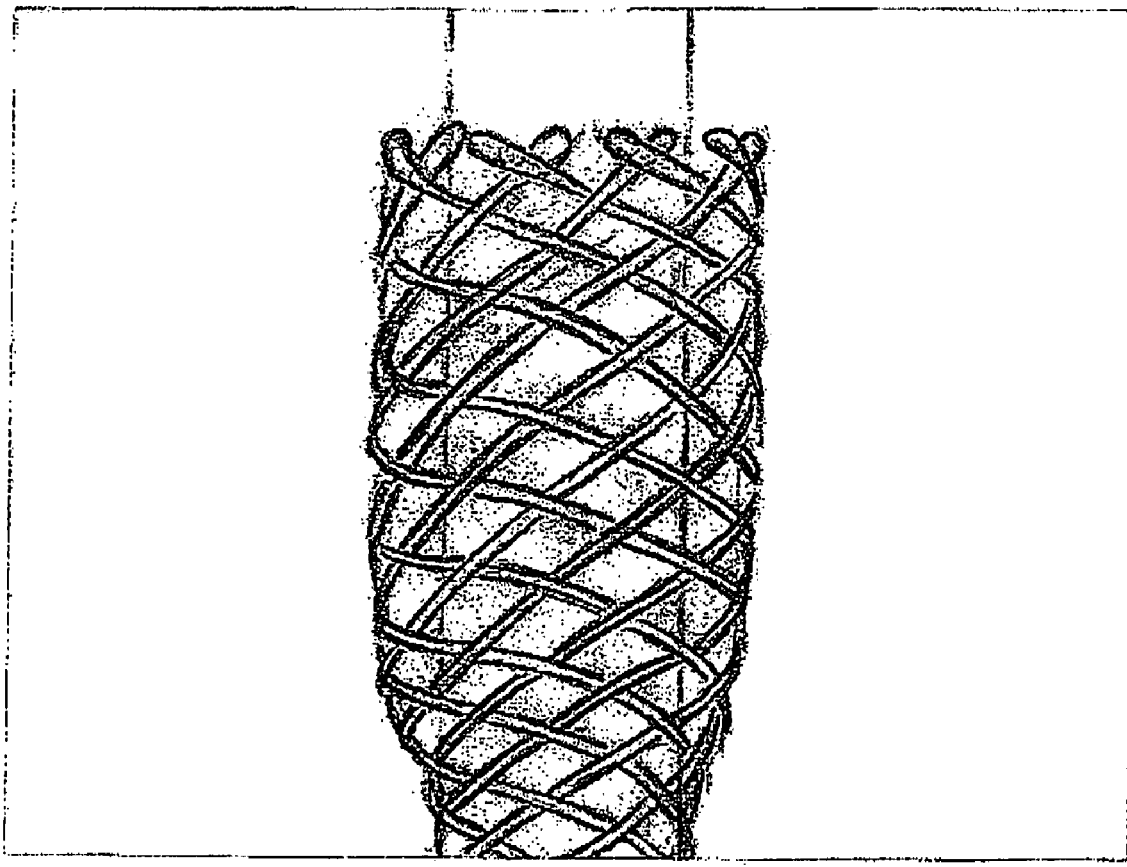
FIG. 5 shows, in another embodiment, the filament profile at the end of the braided stent, in particular at another end (the lower end) of the stent according to FIG. 3. Here too, looped thread formations can be seen, so that no free thread ends protrude at the end.

The thread material used is a polyester monofilament of polyethylene terephthalate (PET) with a filament diameter of 0.3 mm. The braid was formed with a thread intersection angle of 110° over a mandrel of 18 mm diameter. The stent ends diverge radially at both extremities. The diameter of the stent end is 24 mm. See FIG. 3.

EXAMPLE 2

Stent for the Bile Duct Region

The thread material used is a polylactide monofilament of P-L-LA with a filament diameter of 0.3 mm. The braid was formed with a thread intersection angle of 100° over a mandrel of 8 mm diameter. The stent has a constant lumen, that is to say the stent ends do not diverge, and they have a diameter of 8 mm.

EXAMPLE 3

Stent for the Colon Region

The thread material used is a filament of stainless steel type W 1.4310 with a diameter of 0.15 mm. The braid was formed with a thread intersection angle of 90° over a mandrel of 22 mm diameter. The stent diverges radially at one end. The diameter at the stent end is 28 mm.

Production of the implant, in particular of the stent, according to the invention is possible by machine braiding. In a preferred embodiment, a single thread, in particular a monofilament, is laid in mutually parallel longitudinally oriented loops in a tubular arrangement. These loops, each consisting of two parallel threads contiguous to one another, are simultaneously wound alternately right and left and interlaced, resulting in a braided hose or tube of right and left helices which is then fixed, in particular fixed by heat.

The invention claimed is:

1. A tubular implant in the form of a round braid composed of threads of biocompatible material extending in oppositely directed helices and crossing over each other, wherein thread areas located at the tube ends are free from thread ends, and threads present there are guided back into the braid structures,
wherein thread areas at at least one tube end are turned back in a loop shape, forming a U-turn, and are guided back in the same helix,
wherein each helix is made up of at least two threads, in particular two threads lying parallel alongside one another,
wherein at at least one tube end, one thread area is turned back at 60 to 120° and one thread area from the same helix is turned back at 150 to 300° as a cross-over loop, and the looped thread is guided back in the directly contiguous return helix, and the thread turned back only in a U-shape is guided back in the succeeding parallel return helix, wherein the thread areas angled in a U-shape and the thread areas formed as cross-over loops alternate at the tube end and wherein the threads are monofilaments.

2. A tubular implant as claimed in claim 1 in the form of a stent.

3. The tubular implant as claimed in claim 1, wherein the monofilaments have a diameter of 30 μm to 2 mm.

4. The tubular implant as claimed in claim 1, wherein the braid is braided from a single thread (continuous thread).

5. The tubular implant as claimed in claim 1, wherein thread ends lie in the circumferential plane of the round braid.

6. The tubular implant as claimed in claim 1, wherein thread ends lie contacting one another in each case in a helix and in particular point in opposite directions.

7. The tubular implant as claimed in claim 1, wherein the threads are turned back at at least one tube end and are guided back in helical formation in the braid.

8. The tubular implant as claimed in claim 1, wherein thread areas at at least one tube end are turned back at an angle of 60 to 120°, in particular ca. 90° and are guided back in an oppositely directed helix.

9. The tubular implant as claimed in claim 1, wherein thread areas at at least one tube end are turned back at 150 to 300°, forming a cross-over loop, and are guided back in an oppositely directed helix.

10. The tubular implant as claimed in claim 1, wherein it is designed as a lattice and, in the unstressed state, has a lattice width of 0.5 to 8 mm.

11. The tubular implant as claimed in claim 1, wherein, when a helix has a thread count which is an even number, two threads lying along-side one another in each case extend in opposite directions.

12. The tubular implant as claimed in claim 1, wherein the braid structure has a thread profile of 1 over 1, 1 under 1.

13. The tubular implant as claimed in claim 1, wherein the braid structure has a thread profile of 2 over 2, 2 under 2.

14. The tubular implant as claimed in claim 1, wherein, relative to the cross section of the implant, 4 to 16, helices are provided in each helix direction of the oppositely directed helices.

15. The tubular implant as claimed in claim 1, wherein it is braided from serpentine, continuous, parallel, longitudinally directed, tubularly disposed loops.

\* \* \* \* \*

UNITED STATES PATENT AND TRADEMARK OFFICE
CERTIFICATE OF CORRECTION

| | | |
|---|---|---|
| PATENT NO. | : 7,582,108 B2 | |
| APPLICATION NO. | : 10/973824 | |
| DATED | : September 1, 2009 | |
| INVENTOR(S) | : Helmut Hierlemann et al. | |

It is certified that error appears in the above-identified patent and that said Letters Patent is hereby corrected as shown below:

Claim 1, Column 6, Line 54:

Please delete "...structures, ..."

and replace with

-- structure, --

Signed and Sealed this

Seventeenth Day of November, 2009

David J. Kappos
*Director of the United States Patent and Trademark Office*